United States Patent [19]

Drobník et al.

[11] Patent Number: 4,659,849

[45] Date of Patent: Apr. 21, 1987

[54] MACROMOLECULAR COORDINATION COMPOUND CONTAINING PLATINUM WITH ANTITUMOR ACTIVITY IN RODENTS

[75] Inventors: Jaroslav Drobník; Dagmar Nosková; František Rypáček; Marie Metalová; Vladimír Saudek, all of Prague, Czechoslovakia

[73] Assignee: Ceskoslovenska akademie ved, Czechoslovakia

[21] Appl. No.: 796,288

[22] Filed: Nov. 8, 1985

[30] Foreign Application Priority Data

Nov. 9, 1984 [CS] Czechoslovakia ............ 8539-84

[51] Int. Cl.$^4$ .............................................. C07F 15/00
[52] U.S. Cl. ................................................... 556/137
[58] Field of Search ...................................... 556/137

[56] References Cited

U.S. PATENT DOCUMENTS

| | | | |
|---|---|---|---|
| 4,283,342 | 8/1981 | Yolles | 556/137 X |
| 4,376,782 | 3/1983 | Turkevich et al. | 556/137 X |
| 4,551,502 | 11/1985 | Howell et al. | 556/137 X |
| 4,565,884 | 1/1986 | Andrulis, Jr. et al. | 556/137 |
| 4,584,392 | 4/1986 | Smith et al. | 556/137 |

Primary Examiner—Helen M. S. Sneed
Attorney, Agent, or Firm—Leydig, Voit & Mayer

[57] ABSTRACT

A macromolecular compound with antitumor activity in which hydroxy groups in side chains of a polymer have the character of primary, secondary or tertiary alcohols and are completely or in part esterified with carboxyl in the position C4 of 1,2,4-tricarboxybenzene, whereas the carboxyls in positions C1 and C2 bind an atom of platinum with coordination bonded amino ligands.

A method for producing the macromolecular compound consists in acylation of the polymer carrying alcohol groups with chloride anhydride of trimellitic acid of the formula II,

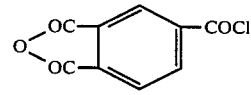

hydrolyzing the anhydride in the subsequent step, and bonding an atom of bivalent platinum carrying an amino ligand to the formed vicinal carboxylic groups.

3 Claims, No Drawings

MACROMOLECULAR COORDINATION COMPOUND CONTAINING PLATINUM WITH ANTITUMOR ACTIVITY IN RODENTS

The invention relates to a macromolecular coordination compound containing platinum with antitumor activity in rodents.

Antitumor compounds, which suppress the growth of cancer cells by affecting the genetic apparatus or metabolism, have altogether undesirable effects on healthy cells and organs. Development of new chemical structures of antitumor compounds tends to increase the ratio between effects on a cancer cell and effects on a healthy cell. However, this ratio depends not only on the structure but also on the concentration of an antitumor compound which comes into contact with both types of cell. Various methods of application of antitumor compounds are used to shift the concentration ratio to a higher concentration in the environs of tumor cells. For example, intraarterial injection into an artery supplying the tumor with blood is used; intraperitoneal administration is used in the case of ascitic forms of tumors; direct charging into the urinary bladder of a solution of antitumor compound is used in the treatment of tumors of the bladder; and, the introduction near a tumor of implants which contain an antitumor compound is used.

But the above methods may be used only in special cases. A more general application could be expected with antitumor compounds having a sufficiently large molecule, which would have a limited penetration through biologic barriers. This could, for example, avoid fast exclusion in urine and the consequent necessity of frequent administration and damage to the kidney. Various forms of antitumor compounds bonded to a polymer have been developed, such as adriamycine, cyclophosphamide, methotrexate, cytosinearabinoside, and the like. However, attempts to prepare a polymeric antitumor compound containing platinum have not been successful, because platinum bonded in such compounds was unable to react with the components of tumor cells in a way required for the antitumor action.

Thus, for example, C. E. Carraher, Jr. described a polymer which has a platinum atom incorporated in the main chain of polymer molecules formed by diamines of the general formula

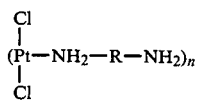

or a platinum derivative, where poly[bis(methylamino)-phosphazene], poly(vinylamine), a copolymer of vinyl amine with vinyl sulfonate, or poly(ethyleneimine) was used as an amino ligand. These polymers have, in addition to the above mentioned disadvantageous reactivity of the platinum atom, another disadvantage consisting in their resistance to biological degradation. Administration of these polymers would cause a danger of their accummulation in the body.

The authors of the present invention have now found that a macromolecular compound, which slowly liberates a low-molecular-mass coordination complex of platinum in a biologic medium thus allowing the said complex to enter cells and act there with an antitumor effect, can be prepared.

According to the present invention, there is provided a macromolecular compound, which polymer, chosen from a group of poly(amino acids), polysaccharides, and polyamides containing alpha-hydroxyacids, contains hydroxyl groups in side chains having the character of primary, secondary or tertiary alcohols and are completely or in part esterified with the C4 carboxylic groups of 1,2,4-tricarboxybenzene, whereas the carboxylic groups at C1 and C2 bind an atom of platinum with coordination-bonded amino ligands represented by two molecules of monoamine selected from the group consisting of ammonia, alkylamine with a linear or branched alkyl chain containing 1 to 6 carbon atoms, and cycloalkylamine with a cycloalkyl group formed from 4 to 7 carbon atoms, or by diamine with a linear or branched chain containing 1 to 6 carbon atoms, or by 1,2-diaminocycloalkane, where the cycloalkane has a cyclic structure containing 4 to 7 carbon atoms, or by diamine of the general formula I,

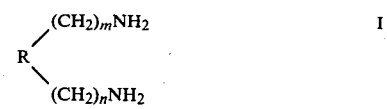

where R is cycloalkylene containing 4 to 7 carbon atoms and m=0,1 or 2 and n=1 or 2.

According to the present invention, there is also provided a method for preparation of the macromolecular compound, wherein a polymer carrying the above said alcohol groups is acylated with the chloride anhydride of trimellitic acid of formula II,

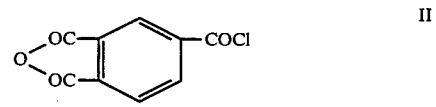

the anhydride is hydrolyzed in the subsequent step, and an atom of bivalent platinum carrying the above mentioned amino ligands is bonded to the formed vicinal carboxylic groups.

An advantage of the macromolecular compound according to the invention is that it can be prepared from macromolecules which are completely decomposed and digested in the body after they split-off the platinum complex. Further advantages are that the molecular mass can be adjusted according to the requirements of therapy, the liberation of the low-molecular-mass complex may be controlled within considerable limits, and the split-off complex can be chosen from compounds for which the antitumor activity has already been proven.

Another advantage of the macromolecular compound according to the invention consists in splitting off the efficient low-molecular-mass platinum complex from the macromolecule in the body, under the assistance of enzymes or without it, by hydolysis of an ester bond between a hydroxyl of a side chain of the polymer and a carboxylic group of trimellitic acid (1,2,4-tricarboxybenzene). It is also advantageous that the stability and thus rate of hydrolysis are easily controlled by the character and surroundings of the corresponding hydroxyls on the polymer. Further merit of the macromolecular compound according to the invention lies in the possibility of choosing the amino ligand from a group consisting of amino ligands which have been proven to be suitable from the aspect of application efficiency, because the type of bonding to the polymer and the splitting rate do not depend on the character of amino ligand. The macromolecular compound according to the invention is also advantageous because it can be prepared from macromolecules which, after splitting off the platinum complex, are completely decomposed and digested; there is no danger of the accumulation of macromolecules, which is connected with undesirable effects on the treated organism. Furthermore, the molecular mass can be advantageously chosen considering the requirements of therapy. Finally, the macromolecule may contain additional chemical groups which desirably affect the transport of macromolecule in the body and thus its therapeutic efficiency.

The following examples, which do not limit the scope of the invention, are illustrative of the method for preparing the compound of the invention.

EXAMPLE 1

Poly[N-(2-hydroxymethyl)-D,L-aspartamide] (1.5 g) was dissolved in 45 ml of N,N-dimethylacetamide and 1.05 g of chloride anhydride of trimellitic acid and 10 ml of pyridine was added. The mixture was stirred for 48 hours at ambient temperature. Then, 10 ml of concentrated acetic acid was added and the mixture was slowly poured into 750 ml of cold acetone. The precipitated substance was washed with acetone and dissolved in 25 ml of water. The pH was adjusted to 5.0 by means of aqueous sodium hydroxide (1 mol.l$^{-1}$ NaOH) and the solution was dialyzed against deionized water for 4 days. The volume of dialysate was adjusted to 25 ml and the amount of bonded 1,2,4-tricarboxybenzene was determined at wave length 283 nm according to a calibration plot. The substitution of 43% hydroxyl groups was attained. The aqueous solution was agitated with 72 ml of an aqueous solution containing 1.4 g of trans-1,2-diaminocyclohexane platinum(II) dinitrate complex for 72 hours at ambient temperature in darkness. Then, it was dialyzed against deionized water for 7 days. The volume after dialysis was adjusted to 40 ml and the content of platinum was determined by the neutron-activation analysis. The content of 1,2,4-tricarboxybenzene was spectrometrically determined in a sample which was diluted with a 5% solution of potassium iodide and allowed to stand for 8 hours. It has been found, that the platinum concentration is 56.4 mmol.l$^{-1}$, the concentration of 1,2,4-tricarboxybenzene is 89 mmol.l$^{-1}$, and the content of dry substance is 67.3 mg/ml. The composition of the dry polymer, which was determined by elemental analysis, is given in table 1.

EXAMPLE 2

Poly[N-(2-hydroxypropyl)-D,L-aspartamide] (1.7 g) was dissolved in 45 ml of N,N-dimethylacetamide and 2.1 g of chloride anhydride of trimellitic acid and 10 ml of pyridine was added. The mixture was stirred for 48 hours at ambient temperature and the polymer was further worked out as in example 1. The acylation of alcohol groups amounted to 39.5%. The polymer solution purified by dialysis was mixed with 50 ml of an aqueous solution containing 1.04 g of trans-1,2-diaminocyclohexane platinum(II) dinitrate complex. After 72 hours, the mixture was dialyzed and analyzed as in example 1. The composition of the polymer is given in table 1.

EXAMPLE 3

Poly[N-(2-hydroxyethyl)-L-glutamine] (1.7 g) was worked out in the same way as the polymer in example 1. The acylation of alcohol groups reached 36%. Therefore, 1.56 g of trans-1,2-diaminocyclohexane platinum-(II) dinitrate complex was used in 75 ml of water. The resulting product had the composition given in table 1.

EXAMPLE 4

Poly[N-(2-hydroxypropyl)-L-glutamine] (1.9 g) was worked out as the polymer in example 2. The acylation occured at 18% of alcohol groups. For platinum bonding, 0.72 g of trans-1,2-diaminocyclohexane platinum-(II) dinitrate complex was used in 35 ml of water. The composition of the product is given in table 1.

EXAMPLE 5

Inulin (1.5 g), which was reprecipitated with acetone and dried, was dissolved in 25 ml of N,N-dimethylacetamide and 2 g of chloride anhydride of trimellitic acid and 8 ml of pyridine was added. After 48 hours of stirring at ambient temperature, the solution was reprecipitated with a tenfold amount of acetone. The product was dissolved in phosphate buffer of pH 5 and dialyzed against deionized water. The volume was adjusted to 25 ml and the spectrophotometric analysis showed 2 mmol of tricarboxybenzene residue in the total amount. An equimolar amount of trans-1,2-diaminocyclohexane platinum(II) dinitrate complex was added and, after two days, the solution was dialyzed again. For the composition of product see table 1.

EXAMPLE 6

Polyamide (1.5 g) of the composition [NH(CH$_2$)$_2$NHCO(CHOH)$_4$CO]$_n$, which was prepared by condensation of 1,2-diaminoethane and mucic (galactaric) acid, was dissolved in 45 ml of N,N-dimethylacetamide and worked out as in example 5. For the composition of product see table 1.

EXAMPLE 7

The polymer carrying residues of tricarboxybenzene was prepared in the same way as in example 1 and treated with 100 ml aqueous solution containing 1.14 g of diammonio platinum(II) dinitrate complex. Further procedure was the same as in example 1. For the composition of product see table 1.

EXAMPLE 8

The polymer carrying the residue of tricarboxybenzene was prepared in the same way as in example 1 and treated with 100 ml of aqueous solution containing 1.22 g of ethylenediamine platinum(II) dinitrate complex. After being worked out as in example 1, the product was obtained. The composition of the product is given in table 1.

EXAMPLE 9

A polymer carrying the residues of tricarboxybenzene was worked out in the same way as in example 1 and reacted with 100 ml of an aqueous solution containing 1.45 g of trans-(1-aminomethyl-1-amino)cyclohexane platinum(II) dinitrate complex under conditions given in example 1. The analysis of the product is given in table 1.

EXAMPLE 10

A polymer carrying the residue of tricarboxybenzene was worked out in the same way as in example 1 and reacted with 100 ml of an aqueous solution containing 1.4 g of cis-[bis(isopropylamine) platinum(II) dinitrate] complex under conditions given in example 1. The analysis of the product is given in table 1.

TABLE 1

Composition of polymer solutions after dialysis and concentration, which were prepared according to examples 1 to 10

| | | Composition of solution | | Representation of monomers[a] | | | Elemental analysis | | | |
|---|---|---|---|---|---|---|---|---|---|---|
| Example | Aminoligand bonded to platinum atom | Dry substance % | Pt content mmol/l | Initial mol. % | TMA mol. % | Pt mol. % | C % | H % | N % | Pt % |
| 1 | trans-1,2-diamino-cyclohexane (DACH) | 6.73 | 56.4 | 57.1 | 15.7 | 27.1 | 42.6 | 4.65 | 11.0 | 16.34 |
| 2 | DACH | 6.23 | 46.5 | 60.5 | 15.6 | 23.9 | 44.8 | 5.06 | 10.8 | 14.54 |
| 3 | DACH | 7.42 | 54.1 | 64.8 | 12.7 | 22.5 | 44.9 | 5.17 | 11.1 | 14.23 |
| 4 | DACH | 6.0 | 33.5 | 82.1 | 3.1 | 14.8 | 47.4 | 6.25 | 12.1 | 10.9 |
| 5 | DACH | 5.3 | 33.5 | 77.2 | 5.6 | 17.2 | 40.1 | 5.3 | 1.77 | 12.33 |
| 6 | DACH | 5.5 | 30.4 | 69.7 | 10.5 | 19.8 | 39.9 | 5.05 | 6.28 | 10.78 |
| 7 | NH3 | 4.1 | 42.7 | 57.1 | 13.6 | 29.2 | 37.2 | 34.45 | 12.14 | 20.35 |
| 8 | 1,2-diaminoethane | 4.4 | 36.4 | 57.1 | 17.6 | 25.2 | 40.8 | 4.54 | 11.5 | 16.15 |
| 9 | 1-aminomethyl-1-aminocyclohexane | 5.1 | 45.8 | 57.1 | 12.5 | 30.4 | 42.6 | 4.76 | 10.8 | 17.34 |
| 10 | isopropylamine | 3.2 | 21.6 | 57.1 | 22.3 | 20.6 | 43.7 | 5.09 | 11.07 | 13.18 |

[a]The unsubstituted monomer is given as "Initial", the monomer acylated with 1,2,4-tricarboxybenzene as "TMA", and the monomer substituted with 1,2,4-tricarboxybenzene carrying a platinum atom with an amino ligand as "Pt"; mol. % is the number of units of the given monomer in 100 monomer units.

EXAMPLE 11

Male SPF-mice weighing 20 g±1 g were administered intrapertoneally the polymer solution prepared according to example 2, which was correspondingly diluted with a 5% solution of glucose. The mice were raised in the standard way and their decay was followed. The dependence of decay on the dose is shown in table 2.

TABLE 2

The decay of male SPF mice depending on the dose of polymer prepared according to example 2 (expressed in nmole Pt per kg of living weight).

| Dose (μmol/kg) | No. of mice in the experiment | Perished | Percent of decay |
|---|---|---|---|
| 168 | 6 | 6 | 100 |
| 121 | 6 | 3 | 50 |
| 84 | 6 | 1 | 17 |
| 42 | 6 | 0 | 0 |

EXAMPLE 12

Male SPF-mice weighing 20±0.8 g were administered through a tail vein
(a) 0.7 μmol of trans-1,2-diaminocyclohexane platinum(II) trimellitate complex in 0.2 ml of 5% glucose,
(b) 0.4 μmol of cis-diammonio platinum(II) dichloride complex in 0.2 ml of physiologic saline,
(c) 0.9 μmol of platinum in the form of the compound prepared in example 3 in 0.2 ml of 5% glucose.
The animals were decapitated at certain time intervals and samples of blood, kidney, liver, spleen, and muscle were withdrawn. The content of platinum in the dry substance was determined. The results are presented in table 3.

TABLE 3

| | Content of platinum in the dry substance (ppm) | | | | | | | | |
|---|---|---|---|---|---|---|---|---|---|
| | Preparation a | | | Preparation b | | | Preparation c | | |
| | 1 h | 6 h | 24 h | 4 h | 8 h | 28 h | 1 h | 6 h | 24 h |
| Blood | 13.9 | 6.56 | 3.71 | 3.1 | 3.2 | 3.8 | 249 | 97.2 | 34.9 |
| Kidney | 27.1 | 12.4 | 24.1 | 13.2 | 31.6 | 52.9 | 13.1 | 11.9 | 57.1 |
| Liver | 8.9 | 13.9 | 10.1 | 16.1 | 8.7 | 95.5 | 12.7 | 12.0 | 98.1 |
| Spleen | 5.2 | 3.2 | 9.5 | 7.8 | 6.3 | 67.1 | 2.8 | 6.0 | 65.1 |
| Muscle | 3.2 | 2.3 | 2.3 | 2.0 | 6.0 | 8.6 | 2.0 | 1.6 | 16.8 |

The macromolecular character of preparation (c) is favourably manifested in the distribution, above all in a long-termed level in blood and a low level in kidney.

EXAMPLE 13

Male mice DBA/2-J were inoculated intraperitoneally (ip) with $10^5$ cells of leukemia P388. The mice were distributed into 4 groups: Reference—untreated mice, TMA—the mice were administered the 1,2-diaminocyclohexane platinum(II) trimellitate complex in a 5% glucose solution adjusted to pH 7.2 with sodium hydrogencarbonate, P1—the mice were administered the polymer prepared according to example 1, and P3—the mice were administered the polymer prepared according to example 3. The polymers were diluted in both cases with water for injections. The survival in days was followed and evaluated as ILS in percent of the reference.

TABLE 4

The effect of preparations upon leukemia P388 evaluated by the length of survival. The preparations were administered ip on the 1st day.

| Group | Dose (μmol Pt/kg) | Average survival day | ILS (%) |
|---|---|---|---|
| Reference | 0 | 20.6 d | 100 |
| P1 | 61.5 | 43.2 | 209.7 |
| P1 | 30.7 | 47.6 | 231.1 |
| P3 | 20.5 | 46.0 | 223.3 |
| P3 | 10.2 | 35.4 | 171.8 |
| Reference | 0 | 20.0 | 100 |
| TMA | 38.6 | 36.26 | 181.3 |
| TMA | 19.3 | 49.0 | 245 |

EXAMPLE 14

Female mice H were administered intraperitoneally (ip) 0.2 ml of an exudate containing $2 \times 10^7$ cells of an ascitic tumor. The reference group was not given any treatment, the group P1 was administered the polymer prepared according to example 1, the group P2 was administered the polymer prepared according to example 2, and the group cDDP was administered a solution of cis-diammine dichloroplatinum (II) complex (cis-platin) in physiologic saline. Each group consisted of 20 animals; ten of them were decapitated on the 10th day after administration and the cellularity of exudate was determined by centrifugation in a capillary tubes (ascitocryt) parallelly with the weight of exudate. Another group of ten animals was allowed to survive. The results are expressed in percent of the reference and are presented in table 5.

TABLE 5

The effect of preparations on ascitic tumors in female mice H. The underscored values are statistically proved (p 0.01).

| Group | Dose ($\mu$mol/kg) | Administration | Weight[a] | Ascitocryt | Survival |
|---|---|---|---|---|---|
| Ehrlich's ascitic tumor | | | | | |
| P1 | 51.5 | ip | 27 | 20 | 107 |
| P1 | 25.6 | ip | 123 | 56 | 132 |
| P2 | 46.6 | ip | 16 | 12 | 68 |
| P2 | 23.3 | ip | 133 | 68 | 95 |
| P2 | 11.6 | ip | 156 | 66 | 112 |
| cDDP | 16.7 | ip | 30 | 15 | 107 |
| cDDP | 8.3 | ip | 70 | 50 | 127 |
| Ascitic mouse sarcoma S 37 | | | | | |
| P1 | 68.4 | ip | 16 | 2.5 | 55 |
| P1 | 34.2 | ip | 32 | 20 | 88 |
| cDDP | 16.7 | ip | 25 | 6 | 99 |
| cDDP | 8.3 | ip | 98 | 50 | 100 |

[a]The weight of ascitus oscillates considerably and tends to increase because the main side effect of platinum cytostatics is the impairment of the liquids and electrolytes balance which is manifested in excessive drinking and connected with the changed function of kidney tubules.

We claim:

1. Macromolecular antitumor compound containing platinum, wherein hydroxy groups in side chains of a polymer, which is selected from a group consisting of comprising poly(amino acids), polysaccharides and polyamides containing alpha-hydroxy-acids, have the character of primary, secondary or tertiary alcohols and are completely or in part esterified with a carboxylic group in the C4 position of 1,2,4-tricarboxybenzene, whereas the carboxyls in the position C1 and C2 bind an atom of platinum with coordination bonded amino ligands represented by two molecules of monoamine selected from the group comprising ammonia, alkylamine with a linear or branched alkyl chain containing 1 to 6 carbon atoms, and cycloalkylamine with a cycloalkyl group formed from 4 to 7 carbon atoms, or represented by diamine of the general formula I,

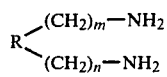

where R is cycloalkylene containing 4 to 7 carbon atoms and m=0,1 or 2 and n=1 or 2.

2. The macromolecular compound according to claim 1, wherein the amino ligand coordination-bonded to the platinum atom is formed from two molecules of a monoamine selected from the group comprising ammonia, alkylamine with a linear or branched alkyl chain containing 1 to 6 carbon atoms, and cycloalkylamine with a cycloalkyl group formed from 4 to 7 carbon atoms, or by diamine with a linear or branched structure containing 1 to 6 carbon atoms, or by 1,2-diaminocycloalkane, where cycloalkane has a cyclic structure containing 4 to 7 carbon atoms, or by diamine of the general formula I,

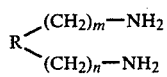

where R is cycloalkylene containing 4 to 7 carbon atoms and m=0,1 or 2 and n=1 or 2.

3. A method for preparation of the macromolecular compound according to claim 1, wherein a polymer carrying alcohol groups is acylated with chloride anhydride of trimellitic acid of formula II,

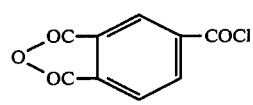

the anhydride is hydrolyzed in the subsequent step, and an atom of bivalent platinum carrying the above said amino ligands is bonded to the formed vicinal carboxylic groups.

* * * * *